United States Patent
Chen et al.

(10) Patent No.: US 8,093,069 B2
(45) Date of Patent: Jan. 10, 2012

(54) FUNCTIONALIZED NITRIDE NANOMATERIALS FOR ELECTROCHEMISTRY AND BIOSENSOR APPLICATIONS

(75) Inventors: Kuei-Hsien Chen, Taipei (TW); Chin-Pei Chen, Yuanlin (TW); Abhijit Ganguly, Calcutta (IN); Li-Chyong Chen, Taipei (TW); Ying-Chin Chang, Taipei (TW)

(73) Assignee: Academia Sinica, Taipei (TW)

( * ) Notice: Subject to any disclaimer, the term of this patent is extended or adjusted under 35 U.S.C. 154(b) by 962 days.

(21) Appl. No.: 12/030,621

(22) Filed: Feb. 13, 2008

(65) Prior Publication Data

US 2010/0279434 A1  Nov. 4, 2010

Related U.S. Application Data

(60) Provisional application No. 60/912,362, filed on Apr. 17, 2007.

(51) Int. Cl.
*H01L 21/00* (2006.01)
(52) U.S. Cl. .................................................. 438/1; 438/3
(58) Field of Classification Search .................. 438/104, 438/1
See application file for complete search history.

(56) References Cited

U.S. PATENT DOCUMENTS

2008/0230716 A1* 9/2008 Tysoe et al. ............... 250/459.1
2009/0219622 A1* 9/2009 Tischler et al. ............ 359/614

* cited by examiner

*Primary Examiner* — Thao P. Le
(74) *Attorney, Agent, or Firm* — Lapus Greiner Lai Corsni, LLC

(57) ABSTRACT

This invention refers to surface modification/functionalization of Nitride nanomaterials and electrochemistry and optical measurement based upon such functionalized Nitride materials. With this invention a variety of bio-molecules such as DNA, protein, and antigens can be immobilized on the surface for measurement to realize ultra-sensitive chemical- and bio-sensing applications.

24 Claims, 5 Drawing Sheets

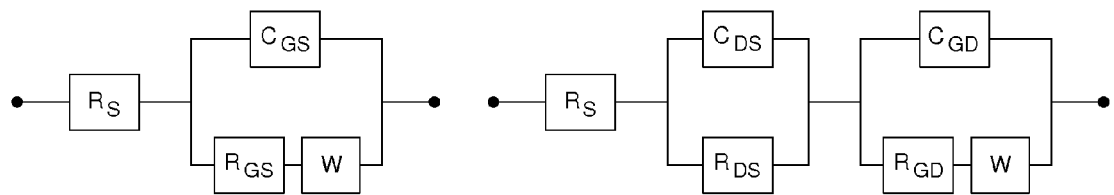
Figure 9A  Figure 9B
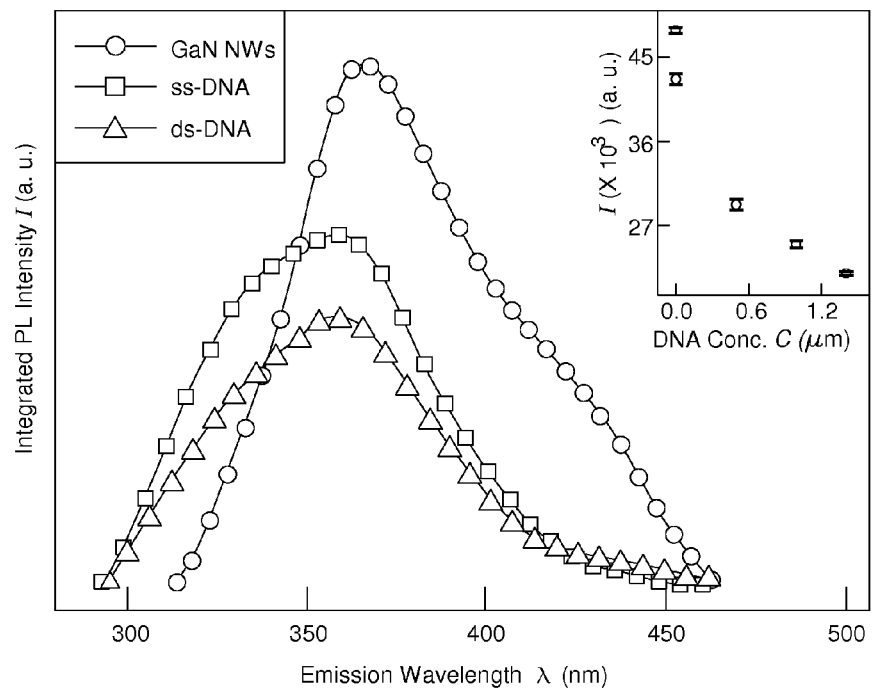
Figure 10

SEQUENCE LISTING

<160> NUMBER OF SEQ ID NOS: 1

<210> SEQ ID NO 1
<211> LENGTH: 12
<212> TYPE: DNA
<213> ORGANISM: Artificial Sequence

```
-continued

<220> FEATURE:
<223> OTHER INFORMATION: Synthetic oligonucleotide

<400> SEQUENCE: 1
cctaataaca at                                                            12
```

FUNCTIONALIZED NITRIDE NANOMATERIALS FOR ELECTROCHEMISTRY AND BIOSENSOR APPLICATIONS

REFERENCE TO RELATED APPLICATIONS

This application claims an invention which was disclosed in Provisional Application No. 60/912,362, filed 17 Apr. 2007, entitled "Functionalized Nitride Nanomaterials for Electrochemistry and Biosensor Applications". The benefit under 35 USC §119(e) of the United States provisional application is hereby claimed, and the aforementioned application is hereby incorporated herein by reference.

BACKGROUND OF THE INVENTION

1. Field of the Invention the present invention generally relates to a methods and system for electrochemistry and biosensor applications, more specifically to functionalized nitride nanomaterials for electrochemistry and biosensor applications.

2. Description of the Related Art

Starting from the date in the discovery of the double helix structure of DNA, the technology of biology has grown from a purely descriptive and phenomenological discipline to that of a set of advanced molecular sciences. Amongst these advanced molecular sciences, bio-sensing is an important area used in such technical areas as clinical diagnosis, medicine, and bioengineering. Sensing single or minuet amount of biomolecules and/or chemicals requires integration of the highly selective recognition properties of biomaterials with unique electronic, photonic, and catalytic features of nanomaterials. Proteins, nucleic acid fragments and their biomolecular complexes have nanometric dimensions comparable with the inorganic nanomaterials, of which the inherently high surface-to-volume ratio offers the opportunity for efficient bio-binding and superb sensitivity in detecting biomoleules. A wide range of nanomaterials and sensing techniques, including absorbance (via surface plasmon), electrochemical or electrical, colorimetry, photoluminescence, and chemiluminescence, are known to have been explored. Though, for decades, several types of materials from metal, silicon to II-VI semiconductors and magnetic materials have attracted immense interest in biotechnology, III-V semiconductors have been left out, despite of same's unique optoelectronic properties and well-known non-toxicity and biocompatibility.

The element carbon is one of the typical widely investigated and heavily studied materials. The form the carbon studied includes graphite, diamond, $C_{60}$, or carbon nanotube. In FIG. 1(a), a depiction of the cyclic voltammograms of Pt, glassy carbon and diamond showing typical potential windows of 0.5, 1.5, and 2.5 Volts are shown respectively. In contrast, FIG. 1(b) depicts the cyclic voltammograms of diamond electrodes with typical potential window less than 2.5 Volts.

A summary of electrochemistry results of the carbon materials is reported by Loh et al. as shown in FIG. 2, in which boron doped diamond exhibits the best performance with the largest potential window and the lowest background current. In summary, a potential window of less than 2.5 Volts is reported for all kinds of electrode materials. More specifically, in FIG. 2, a set of electrochemical potential windows of various electrodes in pH 7 PBS, CV data for boron-doped diamond (BDD), multiwalled carbon nanotube (MWCNT), carbon nanofiber (CNF), and fullerene is depicted.

Nitride materials, with wide and direct band gap, are known to be growing rapidly as a leading optoelectronic material. Recent progress in GaN and InN nanowires (NWs) has attracted huge attention for realizing nanosize ultraviolet or blue emitters, detectors, high-speed field-effect transistors, and high-temperature microelectronic devices. Meanwhile, one-dimensional (1D) nanostructures, with lateral dimensions in the nanometric range, have already been proposed as potential building blocks for the future nanoelectronic devices. Among them, novel nanobioelectronic sensors using the combination of biomolecules with functionalized 1D nanostructures show significant potential.

SUMMARY OF THE INVENTION

The present invention discloses a surface modification and/or functionalization of Nitride NWs and the concomitant electrochemical detection and DNA-sensor applications. A significantly wider potential window up to 4.5 V and very low background current (<0.01 mA/cm$^2$) in the cyclic voltammogram have been demonstrated using such surface modified GaN NW electrodes. A DNA detection limit of $10^{-12}$ M has been achieved. This achievement is far beyond the known detection limit reported to date.

The present invention relates to surface modification/functionalization of Nitride nanomaterials and electrochemistry and optical measurement based upon such functionalized Nitride materials. With this invention a variety of bio-molecules such as DNA, protein, and antigens can be immobilized on the surface for measurement to realize ultra-sensitive chemical- and bio-sensing applications.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 9 is an example of equivalent circuit modeling of the electrode/electrolyte interfaces in accordance with some embodiments of the invention.

FIG. 10 is an example of a photoluminescence sensing in accordance with some embodiments of the invention.

DETAILED DESCRIPTION OF THE PREFERRED EMBODIMENTS

Figure 1A:
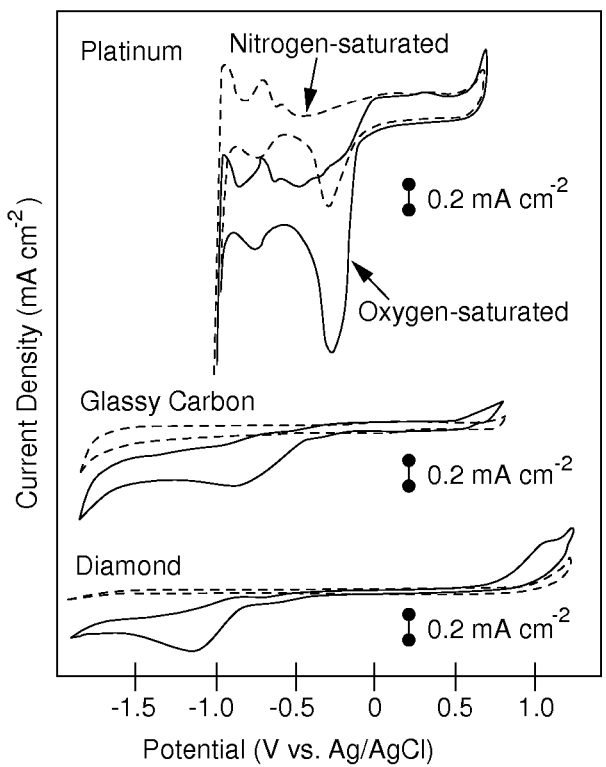
FIG. 1 depicts a first set of prior art carbon characteristics.

Before describing in detail embodiments that are in accordance with the present invention, it should be observed that the embodiments reside primarily in combinations of method steps and apparatus components related to surface modification and/or functionalization of Nitride nanomaterials such as GaN, InN, and AlN. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

referring to FIGS. 3-10, various depictions of the present invention are shown. Based on surface modification and/or functionalization of Nitride nanomaterials such as GaN, InN, and AlN, a method and apparatus are provided for the concomitant electrochemical detection and DNA-sensor applications. The "nanomaterials" include nanowire (NW), nanobelt (NB), nanotip (NT), and nanodot (ND), all of which possess a common feature or characteristic of large surface-to-volume ratio.

Figure 1B:
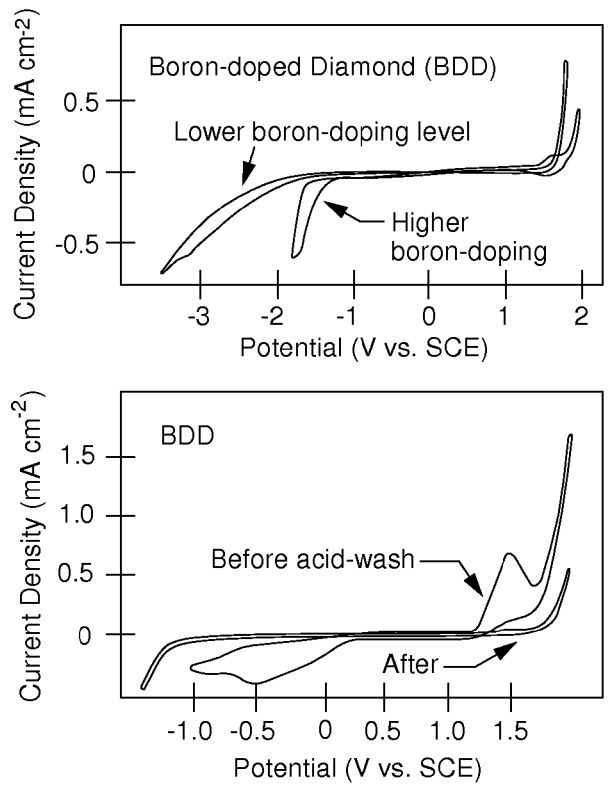
Figure 3:
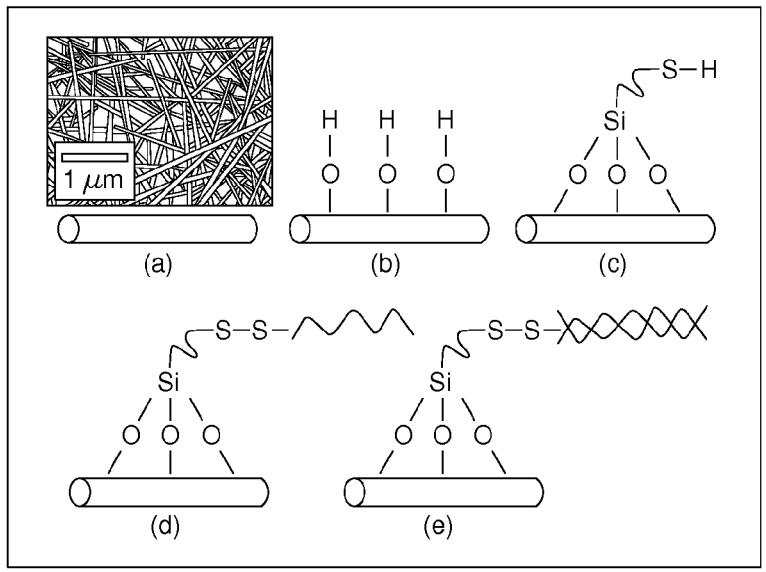
FIG. 3 is an example of schematic diagram of functionalization, immobilization and hybridization process in accordance with some embodiments of the invention.

The Nitride nanomaterials are firstly subjected to organosilane (such as 3-mercaptopropyl trimethoxysilane (MPTS)) modification to enable linkage to biomolecules/chemicals for detection. Secondly, the probe biomolecules such as single-strain DNA (ssDNA) and antigens are linked to the surface of the Nitride nanomaterials via chemical bonding. Finally, the systems are used to sense/detect their counterparts such as the complementary DNAs and antibodies utilizing electrochemistry and/or optical analysis. FIG. 1 shows the schematic diagram of functionalization, immobilization and hybridization process. In FIG. 3, a Schematic diagram of immobilization and hybridization of DNA on GaN NWs is shown. First a GaN is grown and provided (a) or as-grown. The provided or grown GaN is hydroxylated (b). In turn, the hydroxylated GaN is MPTS-modified (c). The modified material (especially the surface) is probe DNA-immobilized (d), and after hybridization, dsDNA-modified GaN NWs is achieved subject to further testing using such schemes as electrochemical detection and DNA-sensor applications (e).

Figure 4:
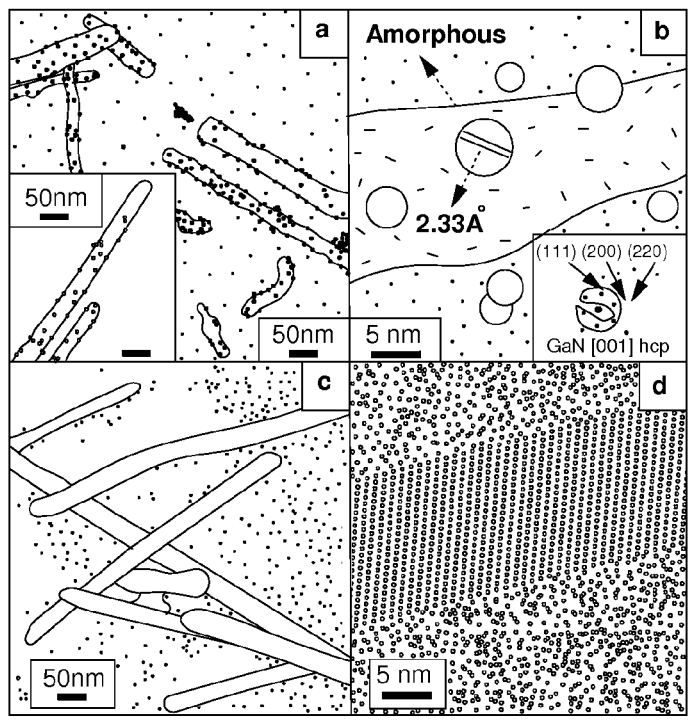
FIG. 4 is an example an organosilane-modified Nitride NWs treated with Au nanoparticles in accordance with some embodiments of the invention.
Figure 5:
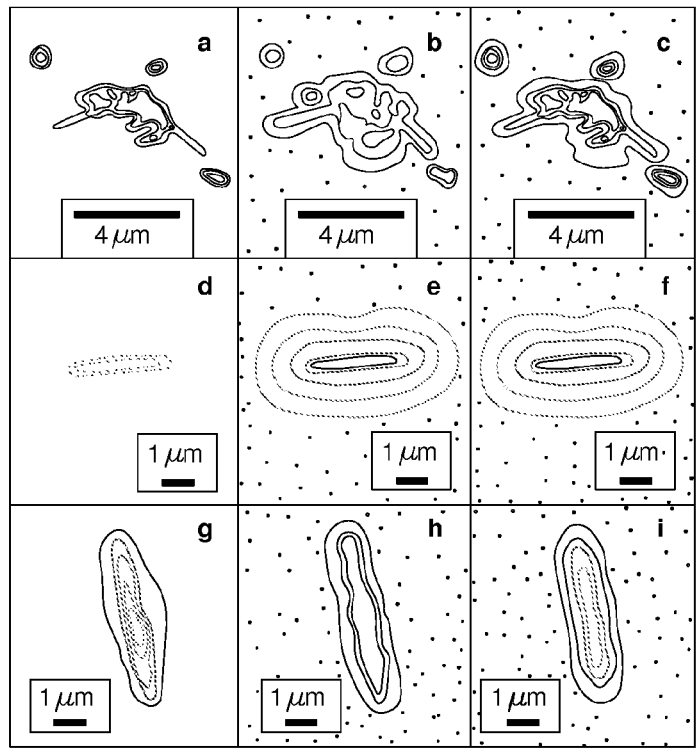
FIG. 5 is an example of a fluorescent image of GaN NWs modified with FAM-labeled ssDNA, along with its corresponding transmitted and the resultant overlapped images in accordance with some embodiments of the invention.

To verify and ensure covalent bonding formation, the organosilane-modified Nitride NWs may be further treated with Au nanoparticles (NPs). Referring to FIG. 4, typical bright-field and dark-field (inset) TEM images are shown (a). HR-TEM image (inset: SAD pattern of Au nanoparticles on the NW) of the Au-MPTS-modified GaN NWs are shown (b). Bright-field TEM image (c) and (d) HR-TEM image of the unmodified GaN NWs (d) are depicted. The size of Au NPs is comparable to that of the ssDNA used in these experiments. X-ray photoelectron spectroscopic (XPS) studies (not shown here) of S2p and Au4f revealed the existence of thiolate and $Au^+$ species, proving the covalent attachment of Au onto the thiol-terminated surface. Moreover, transmission electron microscopy (TEM) image (FIG. 4a) and its corresponding dark-field image (FIG. 4a, inset) reveal a distribution of Au NPs on the surface of MPTS-modified GaN NWs. FIG. 4b shows the high resolution TEM image, confirming the identity of Au NPs, whereas the corresponding selected-area diffraction (SAD) pattern revealed the Au reflection superposed with a typical hexagonal structure of GaN (FIG. 4b, inset). For comparison, FIGS. 4c and 4d represent the images of an unmodified-GaN NWs, which are treated with the same Au NPs, in a similar way as the MPTS-modified ones. No Au NPs are found on unmodified NWs-surfaces.

Referring to FIGS. 5A-5I, confocal Spectral Microscope Imaging System (Leica TCS SP2) may be used for visualization of DNA-immobilization and its hybridization using the FAM (6-carboxyfluorescein)—labeled probe oligonucleotides (ssDNA, 5'DMT-$(CH_2)_6$-S-S-$(CH_2)_6$-CCTAATAA-CAAT-FAM-3' (SEQ ID NO: 1)). FIG. 5a shows a fluorescent image of GaN NWs modified with FAM-labeled ssDNA, along with its corresponding transmitted (FIG. 5b) and the resultant overlapped images (FIG. 5c). The images show clear evidence of oligonucleotides immobilized on the NWs. The corresponding images of unmodified and dsDNA-modified GaN NWs are shown in (d)-(f) and (g)-(i), respectively.

Since the sample is subjected to multiple cleaning and rinsing, the possibility of physisorption of ssDNA on NW-surface can be ruled out. For comparison, the unmodified NWs are directly treated with FAM-labeled ssDNA in a similar fashion. No indication of DNA (FIG. 5d-f) can be observed in this case. Thus, the immobilization of DNA on the NWs surface is indeed established through covalent attachment with MPTS, rather than mere physisorption. In order to verify the hybridization, the probe ssDNAs (without any label) immobilized on NWs are subjected to hybridization with the target DNA (labeled with FAM). Observation of fluorescence from FAM, labeled on target DNA, (FIG. 5g-i) clearly suggests that the ssDNA immobilized on NWs could hybridize efficiently with its complementary strands. The fluorescent images reveal features as small as 1 micron, which can be attributed to small bundle and possibly single NW.

Figure 6A:
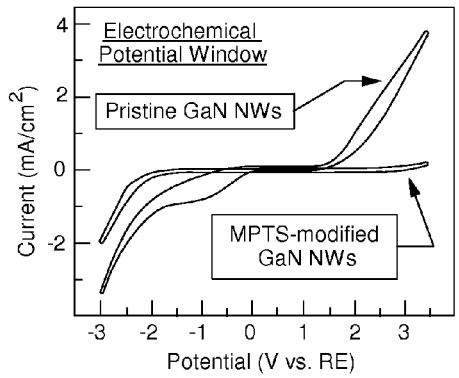
FIG. 6 is an example of a comparison of a pristine GaN NWs sample and a MPTS-modified GaN NWs sampler in accordance with some embodiments of the invention.
Figure 6B:
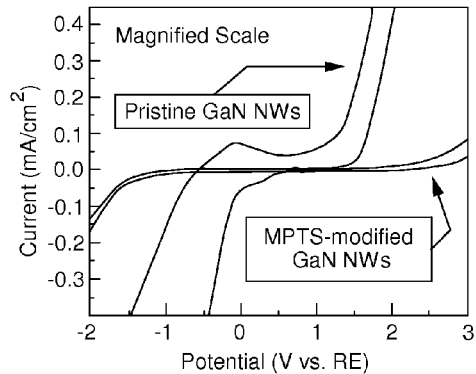

Electrochemical (EC) impedance measurements are carried out with a Solartron analytical 1470E CellTest system in Duplex buffer solution (30 mM Hepes, pH 7.5, 100 mM Potassium Acetate) as background electrolyte. Modified-GaN sample, Ag/AgCl/Sat.KCl, and platinum wire serve as working electrode, reference and counter electrode, respectively and in the same order. As shown in FIG. 6, a comparison of a pristine GaN NWs sample and a MPTS-modified GaN NWs sampler has been made to demonstrate their performance as the electrode for electrochemistry. In FIG. 6, electrochemical potential window of pristine and MPTS-modified GaN NWs electrodes is shown. On the right is the 10 times magnification in the vertical scale and on the left show the low background current.

Figure 2:
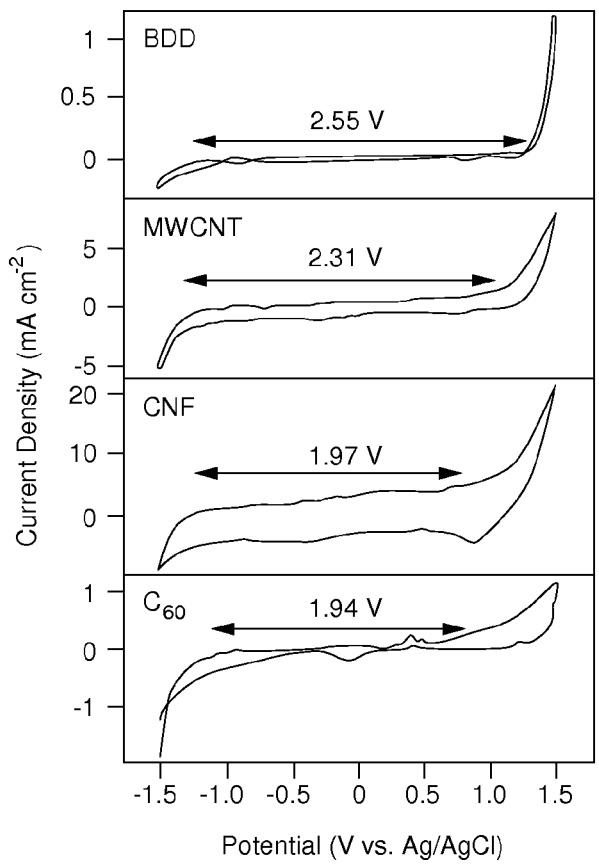
FIG. 2 depicts a first set of prior art carbon characteristics.

It's clear that the MPTS-modified sample provides much wider potential window and lower background current, which is much advantageous for EC measurement. Typically, a potential widow of ~4.5 V and very low background current of ±0.01 $mA/cm^2$ within the potential window have been demonstrated. In contrast to FIG. 1-2 for the BDD, MWCNT, CNF, and $C_{60}$ electrodes, the MPTS-modified GaN NWs electrode outperform all the known rivals, which shed light to ultrahigh sensitive chemical and bio-sensing technique as describe below.

Figure 7A:
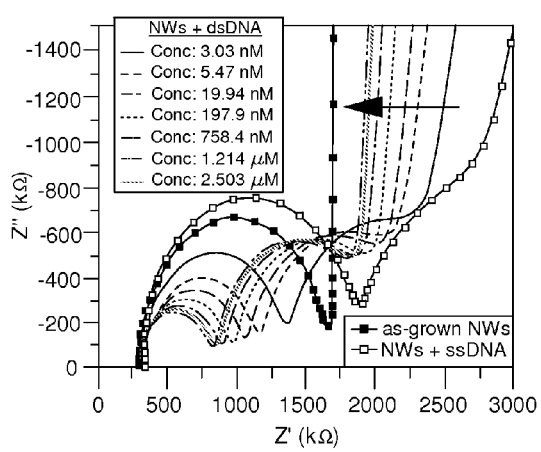
FIG. 7 is an example of an electrochemical sensing in accordance with some embodiments of the invention.
Figure 7B:
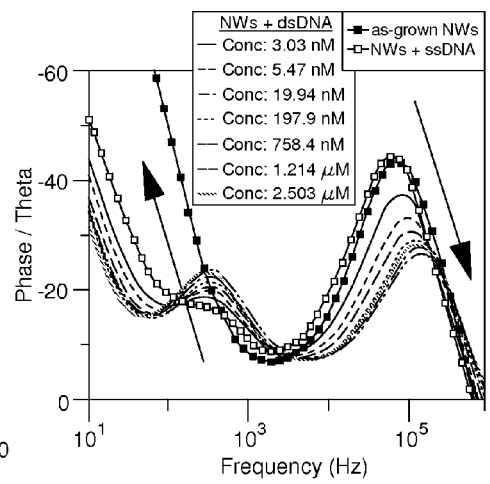

Referring to FIG. 7, electrochemical analysis is shown. Nyquist plots of unmodified, ssDNA-modified and dsDNA-modified GaN NWs (at different concentrations C, in-situ DNA-hybridization results) are shown in FIG. 7(a). Further, corresponding Bode plot is shown in FIG. 7(b). More specifically, FIG. 7a represents the Nyquist plots, imaginary impedance $Z''(\omega)$ vs. real impedance $Z'(\omega)$, of dsDNA-modified NWs sample, along with its corresponded bare NWs and probe ssDNA-immobilized sample. The in-situ DNA-hybridization experiment is performed at every hour, by varying the concentration (C) of target DNA at every 2nd hours. For unmodified (as-grown) GaN NWs sample, the corresponding Nyquist plot exhibits a typical shape of a Faradic impedance spectrum, having a semicircle along with a straight line, which implies that GaN NWs have high impedance and suppressed diffusion-limited electrochemical behavior. It should be noted that no redox marker has been used in the measurement. On immobilization of probe DNA, a significant appearance of a second semicircle region has been observed at the higher Z'-range.

In addition, the Bode plot of FIG. 7b (phase angle vs. frequency) represents the presence of double peaks more prominently. As can be seen, the 2nd peak (P2) at lower frequency region appears after probe DNA-immobilization, indicating the formation of at least one additional capacitive element. DNA-hybridization phenomena lead to the domination of P2 over the original peak (1st peak, P1, at higher frequency side) and thereby consequently reduce the overall impedance. The fact is clear from the increase in relative intensity of semicircle area of P2 over P1 (Nyquist Plots) with the increase in concentration (C) target DNA. In the Bode plot, with increasing C, the increment of P2 can be observed, accompanied by the decrement of P1. A detection limit of 3 nM is demonstrated using the impedance measurement as shown in FIG. 7.

Figure 8A:
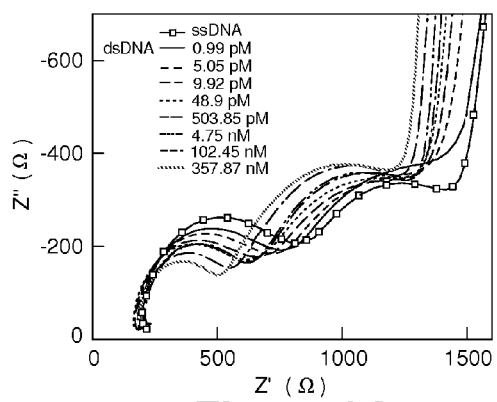
FIG. 8 is an example of an ultra high sensitivity analysis in accordance with some embodiments of the invention.
Figure 8B:
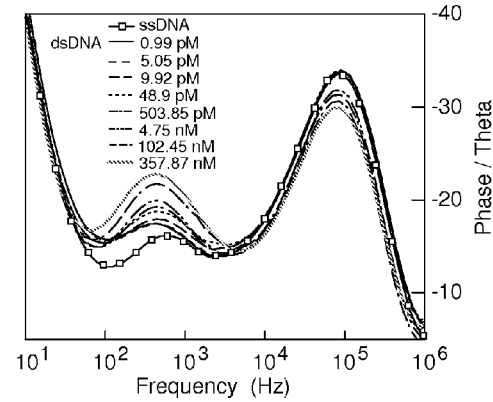

Further measurements have been performed to achieve higher detection sensitivity. Referring to FIG. 8, ultra high sensitivity analysis is performed. Similar to FIG. 7, Nyquist plots (a) and Bode Plot (b) are shown. Howver, note that the Bode plot indicates an ultra low DNA concentration sensing up to $10^{-12}$ M. In FIG. 8, the Nyquist plot and Bode plot of dsDNAs with concentration as low as $10^{-12}$ M (pM) are plotted, wherein it clearly demonstrates the sensitivity up to 1 pM of the impedance measurement utilizing MPTS-modified GaN NWs as electrode.

Referring to FIG. 9, a set of two equivalent Circuit analyses are shown. In element (a), the equivalent circuit model used for unmodified GaN system is shown. In element (b), the same for DNA-modified GaN system is shown. The physical origin of the observed response can be realized by introducing a probable model of the electrode/electrolyte interfaces. For as-grown GaN, a simple, widely used equivalent circuit model (FIG. 9a) can provide the best fit to the data. The data are represented by the ohmic resistance of the electrolyte solution $R_S$; the Warburg impedance W resulting from the diffusion of ions from the bulk electrolyte to the electrode interface; the double layer capacitance $C_{GS}$ of the GaN/electrolyte interface (GS); and electron transfer resistance $R_{GS}$ through the GE. FIG. 9b represents the model that provides the best fit to the data for DNA-immobilized GaN, considering the existence of two interfaces in series, i.e., the GaN/DNA interface (GD) and the DNA/electrolyte interface (DS). The circuit includes the double layer capacitance $C_{GD}$ of GD; and electron transfer resistance $R_{GD}$ through GD; and the capacitance $C_{GS}$ of DS; and resistance $R_{GS}$ at DS.

The fitting results of the Nyquist plot in FIG. 7 are listed in Table 1. The changes of each parameter with respect to the surface modification and immobilization on the GaN-electrolyte interface can be clearly understood. It can be assumed that the immobilization of probe-DNA on GaN surface provides a layer of negative charges creating an additional capacitive element, having its own individual electrical characteristics with an impedance of similar order as our GaN. Consequently, the electron transfer faces double interfaces, DS and GD, in series while transferring from electrolyte to electrode; leading to the formation two individual but mutually dependant impedimetric elements as represented by the peaks P1 and P2 in EIS spectra (FIG. 7). With the formation of dsDNA, as the negative charges accumulate on GaN-surface, the impedance of GaN/DNA (GD) interface is decreasing, indicated by the lowering of peak P1 with the increasing C (FIGS. 7a and 7b). Simultaneously, the increase in DNA molecules provides the continuous rise in space resistance, greatly retarding the diffusion process of electrons from penetrating dsDNA to the GaN NWs, thereby resulting in the dominating nature of DS interface.

From the results (of FIGS. 7-8), it can be pointed out that GaN NWs-system can discriminate the probe-DNA-immobilization and the DNA-hybridization phenomena. Both the Nyquist and Bode plots showed an increase in overall impedance after probe DNA-immobilization, the fact is clearer from in-situ impedance study of ssDNA-immobilization (not shown here). On the contrary, the addition of minute target DNA (C=1 pM) shows a sudden decrease in the overall impedance. However, due to the limitation in the number of binding-sites on the nanometric-surface of NW, the change in impedance spectra shows a saturation level at about C=2 μM. It is worth to mention that the DNA-GaN NWs system of the present invention can respond distinctly to the hybridized DNA, even at a sub-nM concentration level. This implies that oligonucleotides immobilized on the NW-surface can retain their bio-recognition capability.

TABLE 1

Fitting parameters for the equivalent circuit model with different surface immobilization on the GaN NWs.

| | $R_s$ (Ω) | $C_{GS}/C_{GD}$ (F) | $R_{GS}/R_{GD}$ (Ω) | $C_{DS}$ (F) | $R_{DS}$ (Ω) |
|---|---|---|---|---|---|
| Bare GaN | 315.3 | 4.00E−09 | 1467 | | |
| ssDNA | 340.1 | 3.93E−09 | 1519 | 3.92E−07 | 692.8 |
| dsDNA (3.03 nM) | 334.3 | 4.03E−09 | 1014 | 4.43E−07 | 877.4 |
| dsDNA (5.465 nM) | 338 | 3.92E−09 | 816.9 | 4.59E−07 | 891.7 |
| dsDNA (19.94 nM) | 338.6 | 3.90E−09 | 720.8 | 4.73E−07 | 894.8 |
| dsDNA (197.92 nM) | 331.2 | 3.66E−09 | 635.9 | 4.96E−07 | 903.2 |
| dsDNA (758.36 nM) | 323.7 | 3.75E−09 | 570.5 | 5.15E−07 | 902.1 |
| dsDNA (1.214 μM) | 315.1 | 3.98E−09 | 514.7 | 5.34E−07 | 907.6 |
| dsDNA (2.503 μM) | 294.7 | 3.89E−09 | 540.3 | 5.61E−07 | 918.1 |

Room temperature photoluminescence (PL) spectra are obtained using Fluorolog Tau-3 spectrometer and using a 450 W xenon source. FIG. 10 shows the PL spectra, excited at 268 nm (PL excitation peak corresponds to the as-grown GaN NWs). All the spectra are normalized to a reference spectrum from epitaxial GaN film purchased from South Epitaxy Corporation, Taiwan. The unmodified GaN NWs exhibited a broad emission with peak maximum around 365 nm, whereas a prominent quenching behavior is observed after the DNA-immobilization. Luminescence quenching of nano-particles is a useful signal of binding (or adsorption) of molecular species to the particle-surface. For instance, quenching in PL signal of CdS quantum dots-DNA systems has been reported. However, the origin of such quenching is yet to be clarified.

It is also noted that the band-edge emission at 365 nm (for as-grown GaN NWs) is found to be blue shifted to 358 nm, along with the appearance of a prominent shoulder at 330 nm. Furthermore, the blue emission of GaN, which appears as the asymmetric bump around 425 nm in the PL spectrum of the as-grown GaN NWs, is suppressed after the DNA-immobilization. The new band at 330 nm after DNA immobilization is not known to have been reported before. It is suggested that the change of surface states due to the MPTS modification on GaN NW surface may play a role on the fascinating spectral change. Though there is no example, to our knowledge, on the surface passivation effect of MPTS on GaN, the application of organothiol as a self-assembled passivation layer on semiconductor-surface to modify the surface electronic properties is not new for both II-VI and III-V semiconductors. Nevertheless, the blue shift of the band-edge emission at 365 nm, the suppression of the 425 nm band, and the appearance of the 330 nm band, are clearly related to DNA-immobilization, as these changes became increasingly more pronounced with increasing concentration of DNA.

Referring to FIG. 10, PL spectra of unmodified, ss-DNA-modified, and ds-DNA-modified of GaN NWs are shown. The inset shows the correlation of the PL intensity and the concentration of the complementary DNA. As shown in FIG. 10, further quenching of the PL is observed after DNA-hybridization on the GaN NW surface. Slight change of the spectrum in the relative intensities of 330 nm band and the 358 nm band is also observed. All these changes in PL spectra of GaN NWs can be served as signatures for the DNA-immobilization as well as hybridization, thus demonstrating the potential as a new optic-based biosensing technique. Application of ssDNA-GaN NWs system, as a probe in DNA-hybridization process, has been illustrated in FIG. 10 (inset). With the increase in concentration, target oligonucleotides are found to quench the luminescence much more efficiently. The integrated PL intensity, I, (corresponding to band-edge emission from GaN NWs) exhibits a non-linear behavior with the concentration, C, of target oligonucleotides. At high concentration (few tens of $\mu$M), the quenching factor tends to a saturation level due to the limitation in the number of binding-sites on the NW-surface. It is worth to mention that DNA molecules with concentration as low as $10^{-8}$ M could be sensed with relative ease by our DNA-GaN NWs system.

In summary, surface-modified GaN NWs show excellent electrochemical properties such as wide potential windows (up to 4.5 V), and low current background (below 0.01 mA/cm$^2$). The electrodes thus formed have been proven to be effective for the immobilization of ssDNA and dsDNA molecules through covalent binding. Both electrochemical and optical measurements of the GaN NWs, in label-free condition, showed high sensitivity for the immobilization and hybridization of DNAs on the surface. This dual sensing capability can provide detailed information about immobilized bio-molecules and their activity of interaction with a DNA detection limit up to 1 pM, without any appreciable optimization for the sensing-condition.

Furthermore, the procedures of the present invention modifies the subject Nitride nanomaterials for electrochemistry and optical measurement in a few, simple steps. Specifically, the subject Nitride nanomaterials are easily modified for the invention to achieved utro-high sensitivity in measurement (up to $10^{-12}$M). A technique to functionalize or prepares or conditions a GaN surface is provided, thereby allowing for further electrochemical and optical measurement on the GaN surface. The GaN used includes bulk crystalline, thin film, and nano-structured GaN. Each GaN may be subjected to MPTS surface modification prior to DNA attachment. The modified GaN surface may provide a wide potential window for an electrochemical measurement. The surface modified GaN further may provide low background current for electrochemical measurement. In addition, for a surface modified nano-structured GaN, a large surface area may be provided for high sensitivity sensors. The DNA may be thiol-modified to allow subsequent surface attachment.

A covalent bonding may be formed between the thiol-modified DNA oligomers and the MPTS-modified GaN surface. The GaN may be extended to other nitride semiconductors such as InN and AlN. The DNA bonded to the GaN surface may be a selected ss-DNA. The ss-DNA modified GaN surface may be used as a tool to inspect the existence of the complementary DNA.

A sensor utilizing a combination of the technique to functionalize or prepares or conditions a GaN surface and an electrochemical impedance measurement to discriminate the ds-DNA and the ss-DNA modified GaN surface is provided. PL of the DNA modified GaN may be used to further discriminate the ds-DNA and the ss-DNA modified GaN surface. PL intensity from a ds-DNA modified GaN surface may be quenched relative to its ss-DNA modified counterpart. In fact, the GaN surface may be excessively quenched relative to its ss-DNA counterpart. The excessively quenched GaN surface may have PL peak intensity ratio of 330 nm peak and 358 nm peak of the ds-DNA modified GaN surface is relatively much lower relative to its ss-DNA modified counterpart.

In the foregoing specification, specific embodiments of the present invention have been described. However, one of ordinary skill in the art appreciates that various modifications and changes can be made without departing from the scope of the present invention as set forth in the claims below. Accordingly, the specification and Figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A method comprising the step of providing a nitride nanomaterials surface; and the step of providing an organosilane modification on the nitride nanomaterials surface; thereby allowing for immobilization of a probe DNA oligomer, and further electrochemical or optical measurement on the organosilane-modified nitride nanomaterials surface.

2. The method of claim 1 further comprising the step of forming a sensor utilizing a combination of the technique to functionalize or prepares or conditions the organosilane-modified nitride nanomaterials surface and an electrochemical impedance measurement to discriminate a ds-DNA or a ss-DNA modified nitride nanomaterials surface.

3. The method of claim 2 further comprising the step of using hassle-free less-destructive optical-sensing technique via room-temperature PL of the DNA modified nitride nanomaterials to further discriminate the ds-DNA or the ss-DNA modified nitride nanomaterials surface.

4. The method of claim 3 further comprising the step of quenching PL intensity from the ds-DNA modified nitride nanomaterials surface relative to a corresponding ss DNA modified counterpart.

5. The method of claim 4 further comprising the step of excessively quenching PL intensity from the ds-DNA modified nitride nanomaterials surface relative to a corresponding ss-DNA modified counterpart.

6. The method of claim 5, wherein the excessively quenched nitride nanomaterials surface comprising PL peak intensity ratio of 330 nm peak and 358 nm peak of the ds-DNA modified nitride nanomaterials surface thereby having a value that is lower relative to the corresponding ss-DNA modified counterpart.

7. The method of claim 1, wherein the nitride nanomaterials comprises bulk crystallined.

8. The method of claim 1, wherein the nitride nanomaterials comprises nano-structured.

9. The method of claim 1, wherein the nitride nanomaterials comprises thin film.

10. The method of claim 1, wherein the nitride nanomaterials surface provides a wide potential window for an electrochemical measurement.

11. The method of claim 10, wherein the nitride nanomaterials further provides low background current for electrochemical measurement.

12. The method of claim 1, wherein, for the organosilane-modified nitride nanomaterials surface, a large surface area is provided for high sensitivity sensors.

13. The method of claim 2 further comprising the step of forming an ultrasensitive electrochemical-based sensor, even at sub-pM concentration level, without any appreciable optimization for detection-condition.

14. The method of claim 2 further comprising the step of forming a double capacitive layer as a consequence of the immobilization of negatively charged probe-DNA molecules on the nitride nanomaterials surface, and thus the resultant additional capacitive element, forming in series with nitride nanomaterials nanowires, exhibited its own individual electrical characteristics with an impedance comparable to the nitride nanomaterials.

15. The method of claim 1 further comprising the step of forming a sensor utilizing both optical and electrochemical measurements, both in label-free condition, showed high sensitivity, without any little effort to optimize the sensing-condition, for the recognition of target-DNA up to nM and pM of concentrations, respectively.

16. The method of claim 1 further comprising that together with the biocompatibility of the nitride nanomaterials, the label-free dual-sensing techniques opens up great opportunity for ultra-sensitive biosensor applications.

17. The method of claim 1 further comprising the step of forming a covalent bonding between a DNA oligomer and the organosilane-modified nitride nanomaterials surface.

18. The method of claim 17, wherein the organosilane-modified nitride nanomaterials surface comprises a 3-mercaptopropyl trimethoxysilane-modified nitride nanomaterials surface prior to the attachment of the DNA oligomer.

19. The method of claim 17, wherein the DNA oligomer is thiol-modified to allow subsequent attachment to the organosilane-modified nitride nanomaterials surface.

20. The method of claim 17, wherein the DNA oligomer is a selected ss-DNA.

21. The method of claim 20, wherein the selected ss-DNA attached to the organosilane-modified nitride nanomaterials surface is used as a tool to inspect the existence of a complementary DNA.

22. The method of claim 3 further comprising the step of utilizing the inherent luminescence characteristics of the nitride nanomaterials as a tool to monitor the immobilization and hybridization of DNA molecules.

23. The method of claim 22 further comprising the step of utilizing the nitride nanomaterials to monitor the conformational change in the intensity of its own PL resulting from interaction of the probe DNA oligomer with the organosilane-modified nitride nanomaterials surface.

24. The method of claim 22 further comprising the step of utilizing the nitride nanomaterials to monitor the conformational change in the intensity of its own PL resulting from interaction of a target DNA with the probe DNA oligomer.

* * * * *